United States Patent
Baac et al.

(10) Patent No.: US 11,739,188 B2
(45) Date of Patent: Aug. 29, 2023

(54) METHOD FOR MANUFACTURING PHOTOACOUSTIC ULTRASOUND GENERATOR WITH HIGH LASER-INDUCED DAMAGE THRESHOLD AND HIGH-AMPLITUDE ULTRASOUND GENERATOR MANUFACTURED USING THE METHOD

(71) Applicant: Research & Business Foundation Sungkyunkwan University, Suwon-si (KR)

(72) Inventors: Hyoung Won Baac, Anyang-si (KR); Pil Gyu Sang, Suwon-si (KR); Jeong Min Heo, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 280 days.

(21) Appl. No.: 16/991,171

(22) Filed: Aug. 12, 2020

(65) Prior Publication Data

US 2021/0047486 A1 Feb. 18, 2021

(30) Foreign Application Priority Data

Aug. 13, 2019 (KR) .................. 10-2019-0098955

(51) Int. Cl.
*C08J 5/18* (2006.01)
*C08K 3/04* (2006.01)
(Continued)

(52) U.S. Cl.
CPC .............. *C08J 5/18* (2013.01); *A61B 5/0095* (2013.01); *B05D 7/546* (2013.01); *B32B 27/08* (2013.01); *B32B 27/18* (2013.01); *B32B 27/283* (2013.01); *C08K 3/041* (2017.05); *C08L 83/04* (2013.01); *B05D 2201/02* (2013.01); *B05D 2301/00* (2013.01); *B05D 2518/12* (2013.01); *B32B 2250/02* (2013.01); *B32B 2250/24* (2013.01); *B32B 2313/04* (2013.01);
(Continued)

(58) Field of Classification Search
CPC .. B06B 1/00; B06B 1/02; B05D 7/546; B05D 2201/02; B05D 2301/00; B05D 2518/12; C08J 5/18
See application file for complete search history.

(56) References Cited

U.S. PATENT DOCUMENTS 9,601,103 B2 * 3/2017 Guo ........................ G10K 11/36
2014/0112107 A1 * 4/2014 Guo ............................ B06B 1/00
427/596

FOREIGN PATENT DOCUMENTS

CN 109433571 A * 3/2019 ............... B06B 3/00
CN 111112035 A * 5/2020 ............... B06B 1/00
(Continued)

*Primary Examiner* — William P Fletcher, III
(74) *Attorney, Agent, or Firm* — NSIP Law (57) ABSTRACT

A method for manufacturing a photoacoustic ultrasound generator includes forming an uncured prepolymer polydimethylsiloxane (PDMS) film on a substrate, spraying a solution of light-absorbing nano-particles onto a surface of the uncured PDMS film, and then permeating and diffusing the light-absorbing nano-particles into the uncured PDMS film; and curing the uncured PDMS film containing the light-absorbing nano-particles distributed therein to form a composite film of nano-particles and PDMS.

7 Claims, 4 Drawing Sheets

(51) Int. Cl.
  *B05D 7/00* (2006.01)
  *C08L 83/04* (2006.01)
  *B32B 27/08* (2006.01)
  *B32B 27/18* (2006.01)
  *B32B 27/28* (2006.01)
  *A61B 5/00* (2006.01)
  *B82Y 20/00* (2011.01)
  *B82Y 30/00* (2011.01)
  *B82Y 40/00* (2011.01)

(52) U.S. Cl.
  CPC ....... *B32B 2383/00* (2013.01); *B32B 2535/00* (2013.01); *B82Y 20/00* (2013.01); *B82Y 30/00* (2013.01); *B82Y 40/00* (2013.01)

(56) References Cited

FOREIGN PATENT DOCUMENTS

| | | | |
|---|---|---|---|
| KR | 101799075 B1 | * | 11/2017 |
| KR | 1020170088614 A | * | 12/2017 |
| KR | 10-2019-0007312 A | | 1/2019 |

* cited by examiner

| F [mJ/cm²] | 7 | 17 | 27 | 32 | 40 | 56 | 92 | 102 | 124 | 156 | 181 | 256 | 298 | 312 | 379 | 440 |
|---|---|---|---|---|---|---|---|---|---|---|---|---|---|---|---|---|
| C-P |  |  |  | ■ | ■ | ■ | ■ | ■ | ■ | ■ |  |  |  |  |  |  |
| P-C-P 1 |  |  |  |  |  |  |  |  |  | ■ | ■ | ■ | ■ | ■ | ■ | ■ |
| P-C-P 2 |  |  |  | ■ | ■ | ■ | ■ | ■ | ■ | ■ |  |  |  |  |  |  |
| Cr | ■ | ■ | ■ | ■ | ■ | ■ | ■ |  |  |  |  |  |  |  |  |  |

METHOD FOR MANUFACTURING PHOTOACOUSTIC ULTRASOUND GENERATOR WITH HIGH LASER-INDUCED DAMAGE THRESHOLD AND HIGH-AMPLITUDE ULTRASOUND GENERATOR MANUFACTURED USING THE METHOD

CROSS-REFERENCE TO RELATED APPLICATION

This application claims the benefit under 35 U.S.C. § 119 of Korean Patent Application No. 10-2019-0098955 filed on Aug. 13, 2019, in the Korean Intellectual Property Office, the entire disclosure of which is incorporated herein by reference for all purposes.

BACKGROUND

1. Field

The present disclosure relates to a method for manufacturing a photoacoustic ultrasound generator with high laser-induced damage threshold, capable of generating high-amplitude and high-frequency ultrasound using optical energy and an ultrasound generator manufactured using the method.

2. Description of Related Art

Recently, in order to generate high-amplitude and high-frequency ultrasound, ultrasound generation research using photoacoustic effect has been actively conducted. Various photoacoustic transmitter materials, such as metallic coating, metallic nano-particles, graphene flakes, carbon nanofiber, carbon nanosoot, and carbon nanotube (CNT), have been utilized to produce a composite with a polymer with a high coefficient of thermal expansion (e.g. polymethylsiloxane (PDMS)) for the efficient photoacoustic generation of ultrasound.

In particular, the CNT-PDMS composite transmitter fabricated in a planar configuration is capable of generating temporally narrow ultrasound pulses with a broadband bandwidth (e.g. dc to 70 MHz) and high frequency of 70 MHz. In a focal configuration, the transmitter can produce a high peak frequency of 15 MHz or higher and a broad bandwidth over 30 MHz, together with generating high peak amplitudes more than 70 MPa. CNTs can be used as alight absorber, easily allowing up to 100%, depending on its spatial density. Typically, light absorption of 80% or higher is required to achieve high-efficiency transmitters. An absorbed pulsed light energy is converted into instantaneous heat (up to hundreds of degrees C.) which is transferred to the surrounding PDMS with a high coefficient of thermal expansion. Then, such thermal expansion of composite volume leads to temporally confined strong pressure pulses. The CNT-PDMS composite film-based ultrasound generator has been used to achieve high-frequency and high-amplitude pressure sources not only for medical diagnosis but also for non-contact treatment or therapy, the latter of which employs a focal form of CNT-PDMS generator capable of tightly focusing photoacoustic waves down to a point of 100 m or smaller in size to precisely cut or fragment a desired target into a micro size.

The high-frequency ultrasound may obtain high precision due to small acoustic wavelength, but undergo increasingly high attenuation during propagation due to the high-frequency components. The high-frequency (e.g. >10 MHz) ultrasound has significantly higher attenuation than ultrasound of low-frequency on the order of 1 MHz or lower under conditions such as long-distance propagation of several tens of mm or longer, penetration into living tissues, and passage through obstructions (skin, bone, and etc.). Therefore, high-amplitude ultrasound necessitates to compensate for the ultrasound attenuation. In order to generate the high-amplitude ultrasound, the CNT-PDMS transmitter should be able to absorb high laser energy without damage that proportionally increase the output ultrasound strength. Thus, a high level of laser-induced damage threshold (e.g. >about 300 mJ/$cm^2$/pulse) is strongly required. That is, the high mechanical strength of photoacoustic ultrasound generator is essential to achieve the high-amplitude ultrasound output. Therefore, a photoacoustic generator having the high laser-induced damage threshold and the high energy-conversion efficiency at the same time enables to generate the high-amplitude ultrasound ultimately.

The ultrasound amplitude and the mechanical strength depend on the structural properties of film composites and the optical input characteristics. A structure of the composite film may vary depending on a manufacturing method thereof. Conventionally, the CNT-PDMS composite film is manufactured based on various methods such as high-temperature chemical vapor deposition (CVD) and dip-coating methods. The ultrasound output characteristics are greatly affected by concentration and distribution structure of CNT strands within a PDMS matrix.

With existing fabrication methods, for example, using the CVD to fabricate photoacoustic generators, there are limitations in the size and shape of transmitter substrates. Due to the dimensional restrictions in fabrication of wide-aperture (diameter>20 mm) and long-focus photoacoustic lenses, it is difficult to generate high-frequency ultrasound (>10 MHz) and propagate over a long axial range of 15 mm or longer. Upon the above geometrical restriction of photoacoustic lenses, the generated ultrasound undergoes intrinsic attenuation during propagation, which rapidly increases with acoustic frequency. Thus, the focused ultrasound from photoacoustic generators may not reach a location deeper than 10 mm in biological tissues. Therefore, a process technology that is not restricted by substrate dimensions is required.

When manufacturing the photoacoustic ultrasound generators using the CVD method, there is a limitation in which CNT strands may not evenly grow on the lens surface as the area or a curved portion of lens increases. This is because it is difficult to uniformly flow high-temperature gas for growing the CNT on the substrate having a large area or a curvature. As a result, a yield of the photoacoustic generation is reduced when the generators are produced using the CVD method. The generator may not be formed on a large-area and large-diameter lens, thereby causing limitations in manufacturing lenses with long focal lengths. Those shortcomings act as major limitations in application thereof to various research fields using the focused ultrasound. In addition, the CVD method uses a high temperature gas. Thus, the direct film growth on certain substrates (e.g. glass or polymer) is not allowed because the substrates cannot withstand the high-temperature process (~800° C.). This is a limitation in terms of substrate availability. Only special substrates compatible with the high-temperature process, such as fused silica glass or wafer, can be employed in the CVD method for fabrication of photoacoustic generators.

The dip-coating method is advantageous in manufacturing a photoacoustic generator film on an end of an optical fiber with a few hundreds of micrometers in diameter. In this fabrication process, CNT strands can be mixed with a solvent to form a solution. The optical fiber is immersed in the CNT solution and removed therefrom such that CNTs are deposited on the endface of fiber. Then, the optical fiber is immersed in a PDMS solution in the same way and then pulled out therefrom to coat the CNT-PDMS film on the fiber. However, it is difficult to extend this approach to large-size substrates because there is a uniformity problem for areal distribution of CNT strands because dip-coated CNTs may not be uniformly formed on a substrate especially having a deeply curved spherical surface with a low f-number or a large area of several tens of mm or greater.

The candle-soot method burns a glass substrate using a flame from a candle made of paraffin wax to form a soot on the substrate to form carbon nanoparticles. Then, the PDMS solution is deposited on the carbon nanoparticle layer using a spin-coating or a dip-coating method. However, photoacoustic generators made of candle soot are not robust in terms of mechanical strength, so that they are susceptible to high-energy pulsed laser irradiation. The lower mechanical strength limits the maximum-available ultrasound output that increases as the pulsed laser energy increases. This makes them not proper for high-amplitude ultrasound generators and therapeutic applications. Their laser-induced damage threshold values were 30-110 $mJ/cm^2$ which is lower than the CNT-PDMS film produced using a present method proposed according to the present disclosure.

SUMMARY

In one general aspect, a method for manufacturing a photoacoustic ultrasound generator includes: forming an uncured prepolymer polydimethylsiloxane (PDMS) film on a substrate; spraying a solution of light-absorbing nanoparticles onto a surface of the uncured PDMS film, and then permeating and diffusing the light-absorbing nano-particles into the uncured PDMS film; and curing the uncured PDMS film containing the light-absorbing nano-particles distributed therein to form a composite film of nano-particles and PDMS.

The light-absorbing nano-particles permeated and diffused into the uncured PDMS film may be dispersed such that a mean distance between the light-absorbing nanoparticles in the uncured PDMS film is substantially equal to or larger than a thermal diffusion length during the temporal width of an irradiation laser pulse.

A PDMS composite film obtained by dispersing the light-absorbing nano-particles in the uncured PDMS film such that a mean distance between the nano-particles is substantially equal to or larger than the thermal diffusion length may have a laser-induced damage threshold higher than other nano-particle-PDMS composite films including the light-absorbing nano-particles in which they are densely packed with a mean distance smaller than the thermal diffusion length.

The formation of the uncured PDMS film may include the application procedure of a solution of PDMS dissolved in a solvent onto the substrate using drop-casting or spin-coating methods.

The light-absorbing nano-particles may include at least one nanoparticle selected from the group consisting of metallic nano-particles (e.g. Au or Ag), graphene flake, carbon nanotube (CNT), carbon nanofiber, and carbon nanosoot.

The general aspect of the method for manufacturing a photoacoustic ultrasound generator may further include forming an additional PDMS coating layer by applying a PDMS solution on top of the PDMS composite film; and curing the PDMS coating layer.

DETAILED DESCRIPTION

For simplicity and clarity of illustration, elements in the figures. are not necessarily drawn to scale. The same reference numbers in different figures. denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A purpose of the present disclosure is to provide a method for manufacturing a photoacoustic ultrasound generator having a high-amplitude ultrasound output by greatly increasing the laser-induced damage threshold of the photoacoustic ultrasound generator composed of a nanoparticle-PDMS composite film. With the increased laser-induced damage threshold, the photoacoustic ultrasound generator enables to receive and absorb a higher input laser energy without damage or film ablation which is then converted into a thermal energy used for thermo-acoustic generation of a higher-amplitude ultrasound output.

Another purpose of the present disclosure is to provide an ultrasound generator manufactured using the above method.

A method for manufacturing an ultrasound generator in accordance with an example embodiment of the present invention comprises: forming an uncured prepolymer polydimethylsiloxane (PDMS) film on a substrate; spraying a solution of light-absorbing nano-particles onto a surface of the uncured PDMS film, and then permeating the light-absorbing nano-particles into the uncured PDMS film, wherein a distance between the light-absorbing nano-particles in the uncured PDMS film is substantially equal to or larger than a thermal diffusion length during a temporal width of an irradiation laser pulse; and curing the uncured PDMS film containing the light-absorbing nano-particles spatially distributed therein to form a composite film of nano-particles and PDMS.

In one embodiment, forming the uncured PDMS film includes applying a solution of PDMS dissolved in a solvent on the substrate using drop-casting or spin-coating methods.

In one embodiment, the light-absorbing nano-particles include at least one selected from a group consisting metallic nano-particles (e.g. Au or Ag), graphene flake, carbon nanotube (CNT), carbon nanofiber, and carbon nanosoot.

In one embodiment, the PDMS composite film contains the light-absorbing nano-particles at about 0.01 to dozens % by volume, based on a total volume of the composite film.

In one embodiment, the method further comprises: forming a PDMS coating layer by applying an additional PDMS solution on top of the composite film of nano-particles and PDMS; and curing the PDMS coating layer.

An ultrasound generator in accordance with an example embodiment of the present invention comprises: a top PDMS layer; and a bottom layer of carbon nanotube (CNT)-dispersed PDMS composite formed on a substrate, wherein a distance between the CNTs in the PDMS film may be substantially equal to or larger than a thermal diffusion length during a temporal width of an irradiation laser pulse.

Photoacoustic generation of high-amplitude ultrasound requires high spatial density of light-absorbing nano-particles and mechanical robustness that is characterized by laser-induced damage threshold. The laser-induced damage threshold is defined by the input laser fluence absorbed by an irradiated film, i.e., input optical fluence (mJ/cm$^2$)×optical absorption, in which physical damage such as film ablation or crack starts to appear on the film and then degrade acoustic output performance. While high optical absorption (~100%) in photoacoustic generators can be easily obtained by making densely packed light-absorbing nano-particles, this simultaneously has increased a thermal load to the surrounding media (PDMS and substrate) that receive a thermal energy from the heated nano-particles. Thus, the thermal load from the densely packed nano-particles breaks formation of nanoparticles-PDMS composite or composite-substrate bonding. Laser-induced damage threshold values of dip-coating or solution-processed composite generators were as low as 30~110 mJ/cm$^2$/pulse or even lower, thus limiting the ultimately attainable ultrasound amplitude. Existing fabrication technologies do not have any capability to avoid nano-particles from agglomerating themselves or manipulate a spatial distance among nanoparticles to alleviate the thermal load when a particle-to-particle distance is too close, i.e., closer than the heat diffusion length for a temporal width of laser pulse. According to the method for manufacturing the photoacoustic generator described by the present disclosure, the light-absorbing nano-particles are sprayed onto the uncured prepolymer PDMS liquid film. Then, the light-absorbing nano-particles permeate and spread themselves into the uncured PDMS volume to form the PDMS composite film, without staying as agglomerated or densely packed. This permeation step is followed by thermal curing of PDMS to complete the hardened formation of composite. In this manner, the high optical absorption of ~100% is achieved by the light-absorbing nano-particles that are spatially dispersed in the uncured PDMS film such that a mean distance among light-absorbing nano-particles in the uncured PDMS film is substantially equal to or larger than the heat diffusion length (e.g., 10~100 nm for 25 nm thick nano-cylinders) during a temporal width of laser pulse. As compared to the cases of agglomerated or densely packed nano-particles, the above nano-particle permeation into the uncured prepolymer PDMS liquid leads to the use of increased PDMS volume for photoacoustic excitation. This avoids agglomerated or densely packed nano-particles from generating an exceeding amount of thermal energy per volume that causes the physical damage of composite. Therefore, the thermal loading per volume in the composite is reduced by the above nano-particle permeation step and the heat distribution mechanism to the surrounding media (PDMS and substrate). This leads to an increased threshold for laser-induced damage. That is, since an input laser energy which may be received by the composite film of nano-particles and PDMS and converted into a thermal energy without damaging the composite film can be increased according to the higher level of damage threshold, the photoacoustic generator can produce an increased amplitude of ultrasound output. Furthermore, the method for manufacturing the ultrasound generator according to the present disclosure includes an additional step of PDMS coating on top of the composite film fabricated above, which may stably protect the light-absorbing nano-particles from being exposed to an environment out of the PDMS medium.

Figure 1:
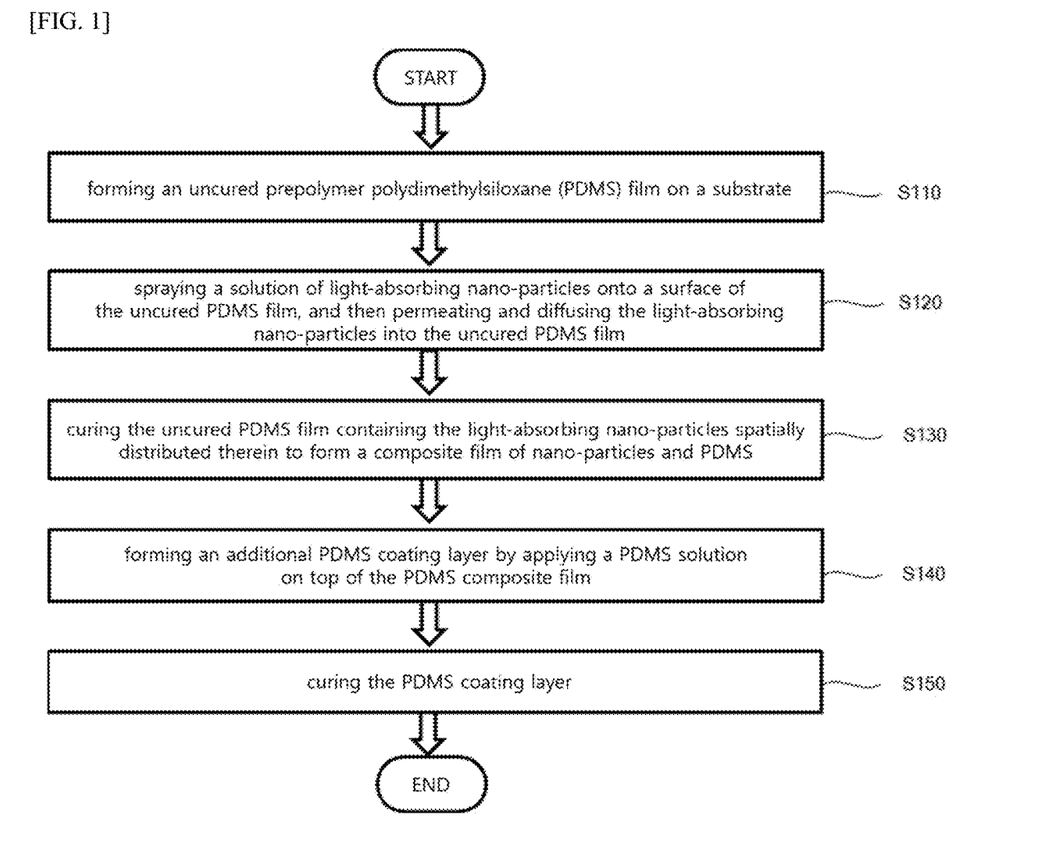
FIG. 1 is a flowchart illustrating a method for manufacturing an ultrasound generator according to an embodiment of the present disclosure.

FIG. 1 is a flowchart illustrating a method for manufacturing an ultrasound generator according to an embodiment of the present disclosure.

Referring to FIG. 1, a method for manufacturing an ultrasound generator according to an embodiment of the present disclosure includes a first step (S110) of forming an uncured PDMS film on a substrate, a second step (S120) of spraying light-absorbing nano-particle dispersed solution on a surface of the uncured PDMS film, and infiltrating the light-absorbing nano-particles into the uncured PDMS film, and a third step (S130) of curing the PDMS film containing the light-to-absorbing nano-particles therein to form a PDMS composite film.

In the first step (S110), the uncured PDMS film may be formed on the substrate by coating a PDMS solution in which PDMS is dissolved in a solvent on the substrate. The solvent may include hexane, diisopropylamine, triethylamine, pentane, or xylene. A method of applying the PDMS solution is not particularly limited. For example, the PDMS solution may be applied on the substrate using a method such as drop-casting or spin-coating method to form the uncured PDMS film. The uncured PDMS film may have a thickness of about 0.1 to 1000 μm.

In the second step (S120), the light-absorbing nano-particle is not particularly limited as long as the nano-particle is capable of absorbing optical energy and releasing heat. For example, the light-absorbing nano-particle may include metallic nano-particles (e.g., Au or Ag), graphene flakes, carbon nanotubes (CNT), carbon nanofibers, and other carbon nanomaterials (e.g., carbon nanosoot). In one example, the light-absorbing nano-particle may include CNTs having a high efficiency of photoacoustic conversion. When constructing the composite using the nano-particle and the PDMS, a high photoacoustic energy conversion efficiency (K) of the order of $10^{-3}$ Pa/(W/m$^2$) or higher may be achieved. Thus, high-amplitude ultrasound generation may be realized. The efficiency (K) is defined based on a following Equation 1.

$$K = \frac{\left|\frac{1}{T}\int_T P(t)dt\right|}{\frac{1}{T}\int_T P(t)dt}$$ [Equation 1]

In the Equation 1, P(t), I(t), and T represent pressure, optical intensity, and period, respectively.

The light-absorbing nano-particles may be sprayed onto an entire surface of the uncured PDMS film. The light-absorbing nano-particles applied on the uncured PDMS film may permeate into the uncured PDMS film due to density difference over time. For example, the light-absorbing nano-particles may be dispersed in toluene, xylene, and the like, and then, the light-absorbing nano-particles solution may be sprayed onto an entire surface of the uncured PDMS film. As described above, when the light-absorbing nano-particles are applied on the entire surface of the uncured PDMS film using the spray method, the light-absorbing nano-particles may permeate inside the uncured PDMS film, such that the light-absorbing nano-particles are spaced apart from one another to decrease the spatial density of the light-absorbing nano-particles. For example, when the light-absorbing nano-particles may be sprayed onto an entire surface of the uncured PDMS film and then the light-absorbing nano-particles may permeate into the uncured PDMS film due to density difference over time, a mean distance of the light-absorbing nano-particles in the uncured PDMS film may be equal to or larger than a thermal diffusion length during a temporal width of laser pulse for photoacoustic excitation. The thermal diffusion length may be defined as a diffusion length of the light-absorbing nano-particle during a time period from a moment at which the light-absorbing nano-particle has a maximum thermal energy to a moment at which the light-absorbing nano-particle has a thermal energy which is 1/e of the maximum thermal energy, in which 'e' is a base of natural logarithm. That is, the thermal energy of the light-absorbing nano-particle may be decreased as the light-absorbing nano-particle is diffused in the PDMS matrix, the thermal diffusion length may be defined as a mean diffusion distance of the light-absorbing nano-particles during the time period from a moment at which the light-absorbing nano-particle has a maximum thermal energy to a moment at which the light-absorbing nano-particle has a thermal energy which is 1/e of the maximum thermal energy. When a distance between the light-absorbing nano-particles in the PDMS film is substantially equal to or larger than the thermal diffusion length, the PDMS film including the light-absorbing nano-particles may have an increased durability against heat-induced damage.

In one embodiment, the light-absorbing nano-particles may be dispersed inside the uncured PDMS film at a concentration which is the same as or smaller than dozens % by volume. For example, the light-absorbing nano-particles may be dispersed inside the uncured PDMS film at a concentration of about 0.01 to 50.0% by volume. In general, an increase in the concentration of the light-absorbing nano-particles may increase the light absorption and increase the output ultrasound amplitude. However, the increase in the concentration of the light-absorbing nano-particles may cause agglomeration of the nano-particles to deteriorate the ultrasound generation efficiency. When the agglomeration of the nano-particles occurs, the particles may grow closer to micro-particles rather than nano-particles, and the surrounding PDMS volume per particle may not be consistently distributed between the nano-particles.

As a result, although a low-energy laser pulse is incident thereon and absorbed thereby, the thermal energy generated therefrom can be not rapidly dispersed around the nano-particles and rather accumulates, thereby causing a mechanical fracture of the nano-particle-PDMS composite. In addition, when micro-scale light-absorbers may be formed by the agglomeration of the nano-particles, a specific heat capacity these micro-scale light-absorbers drastically increases as compared to that of the nano-particles, thus resulting in a rapid decrease in the efficiency of thermoacoustic energy conversion of the surrounding PDMS. Thus, the advantage of the nano-particles-based photoacoustic ultrasound generator may not exhibit.

In the third step (S130), the uncured PDMS film may be cured using heat. For example, the uncured PDMS film may be cured for about 1.5 to 2.5 hours on a hot plate at a temperature of about 85 to 95° C. When the uncured PDMS film has been cured, the PDMS composite film in which the light-absorbing nano-particles are uniformly dispersed in the PDMS may be formed In another example, the method for manufacturing the ultrasound generator according to an embodiment of the present disclosure may further include a fourth step (S140) of forming a PDMS coating layer by applying a PDMS solution on the PDMS composite film and a fifth step (S150) of curing the PDMS coating layer.

Some of the light-absorbing nano-particles in the PDMS composite film formed in the second step (S120) and the third step (S130) may be exposed out of the PDMS film surface. As such, when some of the light-absorbing nano-particles are exposed to an environment out of the PDMS film, the thermal energy generated from the exposed light-absorbing nano-particles may not be transmitted to the PDMS medium, such that the efficiency of the ultrasound generation is deteriorated due to decrease in the intensity of ultrasound as generated.

Thus, in accordance with the present disclosure, in order to solve this problem, the fourth step (S140) and the fifth step (S150) may be further included.

In the fourth step (S140), the PDMS solution may be a solution in which PDMS is dissolved in hexane. The PDMS solution may be applied on the PDMS composite film surface using a method such as drop-casting or spin-coating method to form the PDMS coating layer.

In the fifth step (S150), the PDMS coating layer may be cured using heat. For example, the PDMS coating layer may be cured for about 1 hour on a hot plate at a temperature of about 100° C. The PDMS curing may be also performed at a room temperature for 1~3 days.

According to the method for manufacturing the ultrasound generator according to the present disclosure, the light-absorbing nano-particles are sprayed onto the uncured PDMS film and the light-absorbing nano-particles permeate into the uncured PDMS film to form the PDMS composite film due to density difference over time. Thus, the light-absorbing nano-particles may be dispersed in the uncured PDMS film such that a distance between the light-absorbing nano-particles in the uncured PDMS film is substantially equal to or larger than a thermal diffusion length during a pulse time width of an irradiation laser. When the light-absorbing nano-particles permeate into the uncured PDMS film to form the PDMS composite film, the PDMS composite film has a spatial density of the light-absorbing nano-particles which is slightly lower than those of conventional composite films which are manufactured by forming a coating layer containing the light-absorbing nano-particles on a solid substrate, such as a cured PDMS substrate, a glass substrate, and etc. Thus, as compared to the conventional composite films, in the PDMS composite film in accordance with the present invention, a volume of the PDMS matrix receiving a thermal energy generated by the light-absorbing nano-particles may be increased, and thus the thermal energy received without damaging the composite film or the ultrasound generator may be increased. As a result, a laser-induced damage threshold of the ultrasound generator may be increased, and thus the input laser energy fluence available for ultrasound generation may be increased. When a laser pulse width of 5 to 20 ns is irradiated, it is measured that the conventional composite film has a laser-induced damage threshold of about 30 to 110 mJ/cm$^2$, and the composite film of the present invention has a laser-induced damage threshold which exceeds about 300 mJ/cm$^2$. Therefore, since the PDMS composite film of the present invention can receive a higher laser energy fluence and convert it into a thermal energy without damaging the composite film than the conventional composite films, the PDMS composite film may generate higher-amplitude ultrasound. Further, according to the method for manufacturing the ultrasound generator according to the present disclosure, the light-absorbing nano-particles may be stably prevented from being exposed to an environment out of the PDMS medium.

Hereinafter, specific present examples and comparative examples of the present disclosure will be described. However, the following specific present examples are only some embodiments of the present disclosure, and the scope of the present disclosure is not limited to the specific present examples below.

Present Example

An uncured PDMS film having a thickness of about 20 μm was formed on the glass substrate by drop casting a PDMS solution in which PDMS is dissolved in hexane on the substrate at room temperature. Subsequently, the CNT-dispersed toluene solution was applied on an entire surface of the uncured PDMS film using a spray gun, and then a period of time has lapsed such that the CNT was soaked into the uncured PDMS film. Subsequently, the uncured PDMS film impregnated with the CNT was cured for 2 hours on a hot plate at a temperature of 90° C. Subsequently, a PDMS solution was applied to an entire surface of the cured PDMS composite film via spin coating, and then was cured on a hot plate at a temperature of 90° C., thereby to manufacture an ultrasound generator. A final PDMS composite film had a thickness of about 35 μm.

Comparative Example 1

The CNT-dispersed toluene solution was applied on an entire surface of a glass substrate using a spray gun, and then toluene was vaporized at room temperature so that only CNT remained on the substrate. Subsequently, a PDMS solution in which PDMS is dissolved in hexane was applied on the CNTs placed on the surface of the substrate using a spin coating scheme, and then cured for 2 hours on a hot plate at a temperature of 90° C., thereby to manufacture an ultrasonic generator. A thickness of the PDMS composite film was the same as that of the PDMS composite film of Present Example.

Comparative Example 2

After forming an uncured PDMS film having a thickness of about 20 μm by drop-casting a PDMS solution in which PDMS was dissolved in hexane on a glass substrate at room temperature, the uncured PDMS film was cured for 2 hours on a hot plate at a temperature of 90° C. Subsequently, a CNT-dispersed toluene solution was sprayed onto an entire surface of the cured PDMS film using a spray gun. Subsequently, the PDMS solution was again coated on the CNT-dispersed toluene solution layer on the PDMS film using spin coating. Then, a curing was carried out using a hot plate at a temperature of 90° C., thereby to manufacture an ultrasound generator. A final PDMS composite film had the same thickness as that of the PDMS composite film of Present Example.

Comparative Example 3

An ultrasonic generator was manufactured by forming a 100 nm thick chromium (Cr) film on a glass substrate.

Experimental Example

Figure 2A:
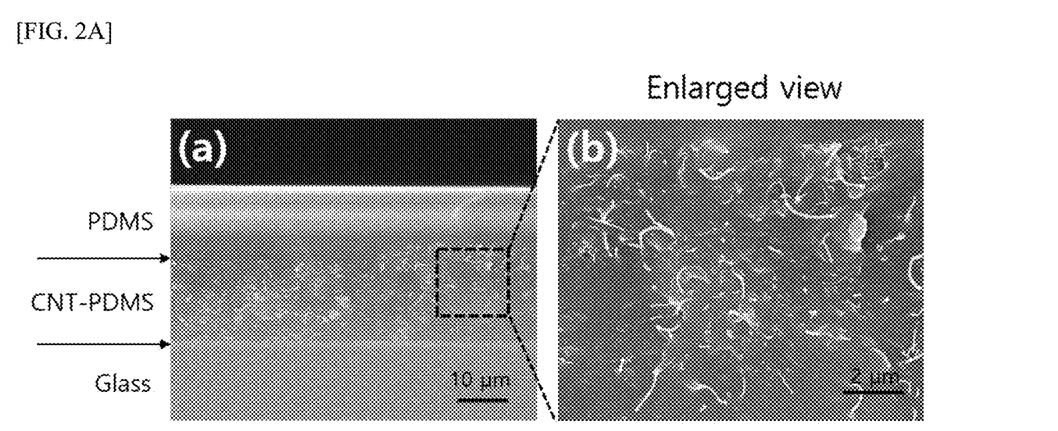
FIG. 2A to FIG. 2C are respective images showing cross sections of CNT-PDMS composite films manufactured according to Present Example, Comparative Example 1 and Comparative Example 2.
Figure 2B:
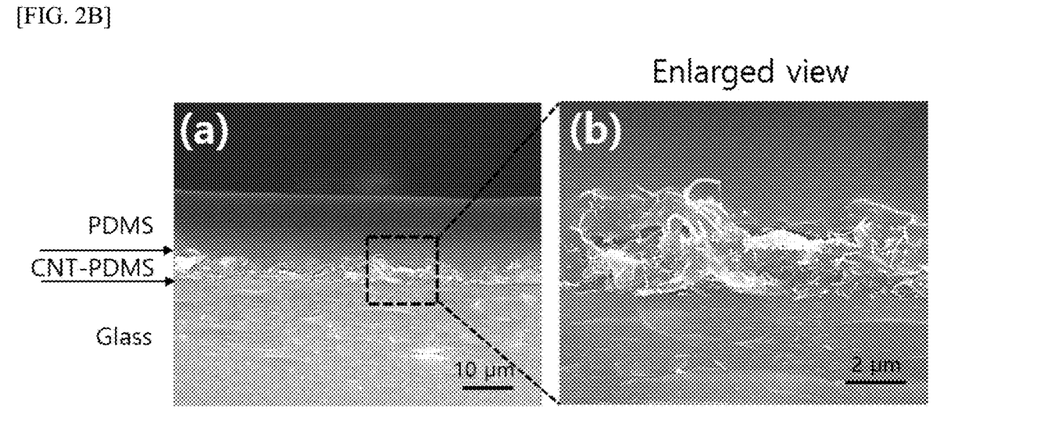
Figure 2C:
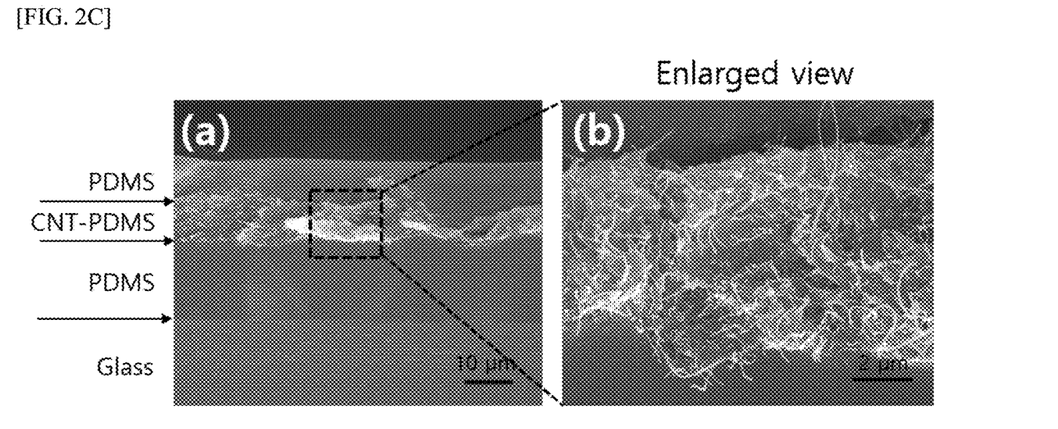

FIG. 2A to FIG. 2C are respective images showing cross sections of CNT-PDMS composite films manufactured according to Present Example, Comparative Example 1 and Comparative Example 2.

Referring to FIG. 2A, it may be identified that in the CNT-PDMS composite film manufactured according to the Present Example, the CNT strands are evenly distributed inside the PDMS medium along a thickness of about 20 μm thereof, and each CNT strand is surrounded with the PDMS. Thus, the CNT may absorb light and transfer the converted thermal energy to PDMS in a reliable manner.

Referring to FIG. 2B, it may be identified that in the CNT-PDMS composite film manufactured according to Comparative Example 1, CNT strands are densely arranged along a thickness of about 6 μm of the PDMS medium from a bottom of the PDMS medium. This results from the fact that the PDMS solution was applied in a state in which the CNT strands were highly densely arranged, such that PDMS did not penetrate into between the CNT strands.

Referring to FIG. 2C, it may be identified that in the CNT-PDMS composite film manufactured according to Comparative Example 2, the distribution volume of CNTs in the PDMS medium may be smaller than that of the CNT-PDMS composite film manufactured according to the Present Example.

Further, it may be identified based on a result of measuring the light absorption of each of the CNT-PDMS composite films shown in FIG. 2A to FIG. 2C, that all films satisfy more than 90% of optical absorption. This means that all of the CNT-PDMS composite films contain a sufficient amount of CNT to absorb light.

Figure 3A:
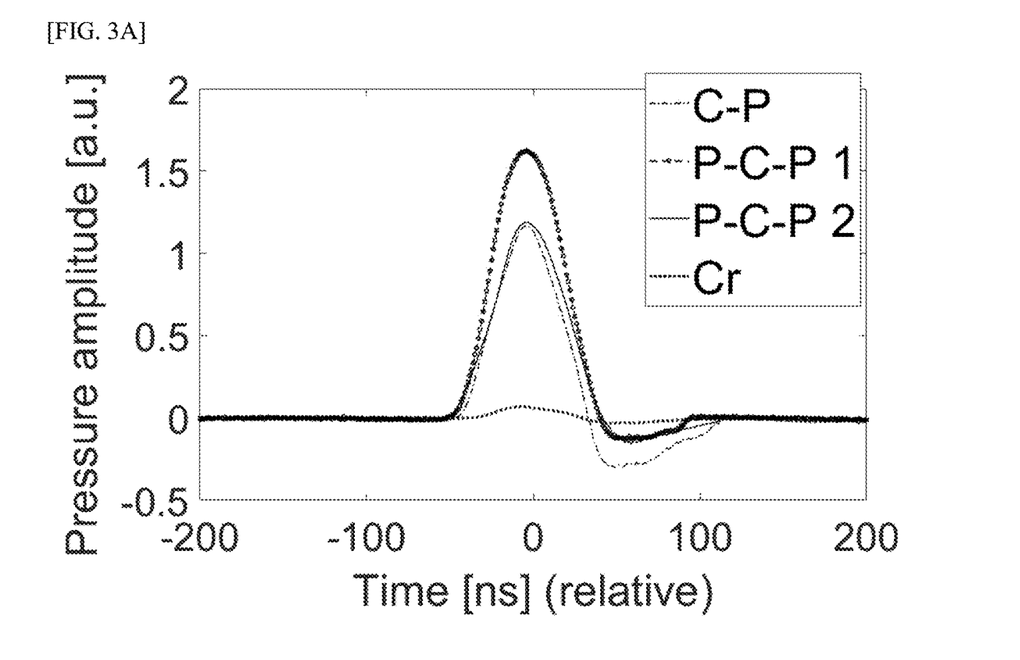
FIG. 3A and FIG. 3B are respective graphs showing ultrasound intensity over time and ultrasound amplitude based on frequency as measured for ultrasound generators manufactured according to Present Example (P-C-P1), Comparative Example 1 (C-P), Comparative Example 2 (P-C-P2) and Comparative Example 3 (Cr).
Figure 3B:
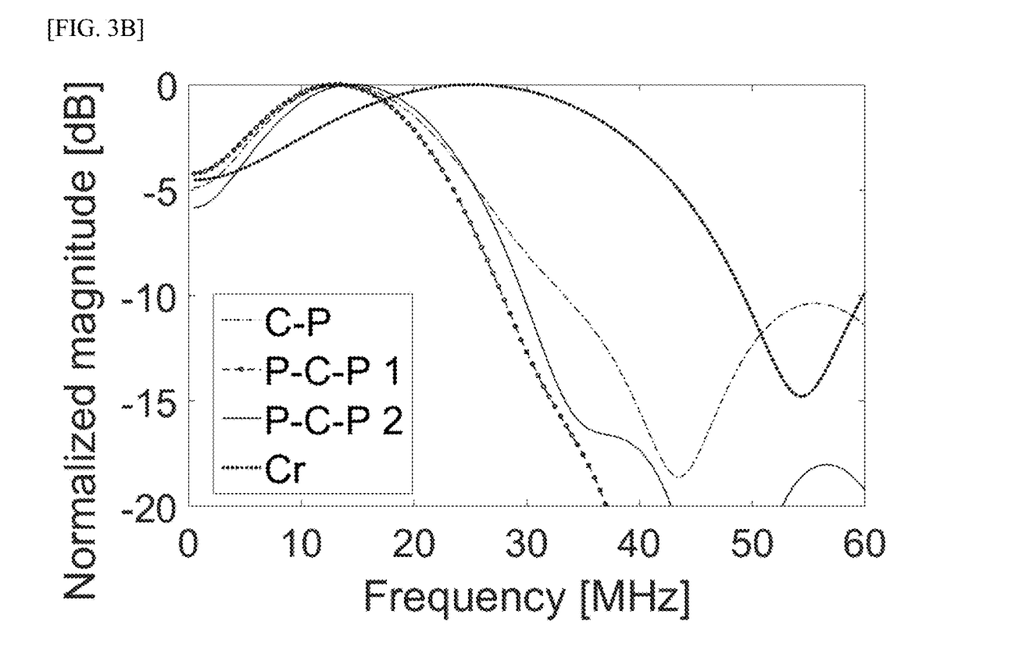

FIG. 3A and FIG. 3B are respective graphs showing photoacoustic waveforms and frequency spectra as measured for photoacoustic generators manufactured according to Present Example (P-C-P1), Comparative Example 1 (C-P), Comparative Example 2 (P-C-P2) and Comparative Example 3 (Cr). The input laser beam generated from an Nd:YAG-pulsed laser source (pulse width 6 ns) was irradiated onto the photoacoustic generators. Ultrasounds generated from the photoacoustic generators were measured using a needle-shaped piezo-electric hydrophone with 1-mm sensing diameter.

Referring to FIG. 3A and FIG. 3B, it may be identified that the photoacoustic generator (P-C-P1) of Present Example generates ultrasound having an amplitude higher by 1.3 times than those of photoacoustic generators (C-P, and P-C-P2) of Comparative Examples 1 and 2. It is also higher by 23.8 times than that of the photoacoustic generator (Cr) of Comparative Example 3. This is because in the photoacoustic generator (P-C-P1) of Present Example, the CNTs are dispersed in the PDMS medium such that a mean distance between the CNTs is substantially equal to or larger than a thermal diffusion length during a pulse time width of an irradiation laser, and thus the heat generated by the light-to-heat conversion of the CNTs can be uniformly transferred to the surrounding PDMS medium around the CNTs. In the photoacoustic generator (P-C-P1) of Present Example, the heat generated by the CNT strands is effectively transferred to the PDMS medium and thus the thermal expansion volume of the PDMS medium per a CNT strand increases, compared to the photoacoustic generators (C-P, and P-C-P2) of Comparative Examples 1 and 2.

The frequency characteristics of the photoacoustic generator are determined based on the thickness of optical absorption within the photoacoustic generator and a pulse width of the incident laser beam. In this experiment, the pulse width of the incident laser beam is fixed. Thus, the difference between the generated ultrasound frequencies mainly depend on the thickness of optical absorption. In the photoacoustic generator of Comparative Example 3, the chromium (Cr) film was 100 nm thick, and thus the highest frequency characteristic from 6 dB to 46 MHz was exhibited. The CNT-PDMS composite films of the photoacoustic generator (PC-P1) of Present Example 1 and the photoacoustic generators (C-P, and P-C-P2) of Comparative Examples 1 and 2 had the thickness in a range of 30 to 40 μm. Thus, the photoacoustic generator (PC-P1) of Present Example 1 and the photoacoustic generators (C-P, and P-C-P2) of Comparative Examples 1 and 2 exhibited similar frequency components, that is, 24.5 MHz, 27 MHz, and 26.5 MHz respectively.

Figure 4:
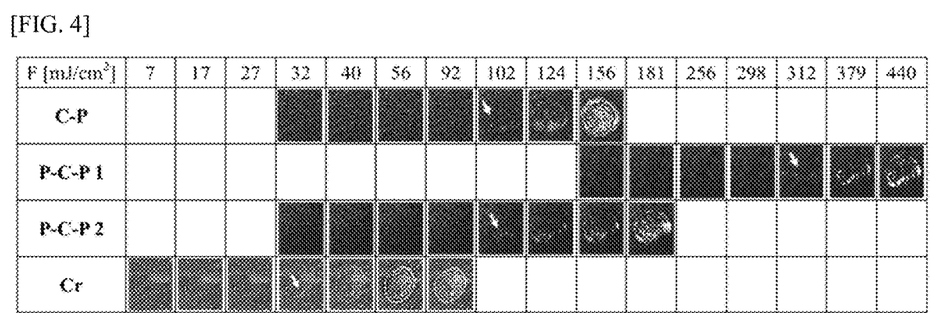
FIG. 4 shows images of results of measuring film damage of the ultrasound generator based on the input laser fluence as irradiated thereto.

FIG. 4 shows images of results of measuring film surface damage of the photoacoustic generator based on the input laser energy fluence as irradiated thereto. In the photoacoustic generator, the mechanical strength to withstand the incident laser energy is a key factor that determines laser-induced damage threshold. Since the ultrasound amplitude increases as the incident optical fluence increases, a high laser-induced damage threshold may lead to generation of the ultrasound having a higher amplitude. In this connection, in FIG. 4, it was found that a surface of the film was damaged at the laser fluences as indicated in yellow.

Referring to FIG. 4, in the films of the photoacoustic generators (C-P, and P-C-P2) of Comparative Examples 1 and 2, the film surface of the generator began to be damaged at the laser fluence of 102.8 $mJ/cm^2$. In the film of the photoacoustic generator (Cr) of Comparative Example 3, the film surface of the generator began to be damaged at a fairly low laser fluence of 32.48 $mJ/cm^2$.

To the contrary, in the photoacoustic generator (P-C-P1) of Present Example, the film surface of the generator began to be damaged at the laser fluence of 312.1 $mJ/cm^2$. This means that the film of the photoacoustic generator (P-C-P1) of Present Example has a laser-induced damage threshold higher by 3 times or greater than those of other CNT-PDMS films of Comparative Examples 1 and 2, and higher by 9.8 times than the laser-induced damage threshold than the Cr film of Comparative Example 3. This is because in the photoacoustic generator (P-C-P1) of Present Example, the CNTs are dispersed such that the mean distance between the CNTs is substantially equal to or larger than a thermal diffusion length during the temporal width of laser pulse; thus, the heat generated by the light-to-heat conversion of the CNTs can be uniformly transferred into the peripheral PDMS medium; and therefore a heat capacity received by the PDMS composite film and the ultrasound generator of Present Example without damage can be increased. As compared to a PDMS composite film in which the CNTs are uniformly dispersed in the PDMS medium, a PDMS composite film in which the CNTs are relatively less uniformly dispersed in the PDMS medium may have a decreased heat energy capacity, which can be received by the PDMS composite film without thermal damage, because when the thermal energy generated by the less uniformly dispersed CNTs makes local temperature variation within the PDMS composite film. In a medium, the heat diffusion caused by the thermal deposition by the CNTs can be expressed as Equation 2 below, and the thermal diffusion length (d) in the medium can be expressed as Equation 3 below.

$$\frac{\partial T}{\partial t} = \chi \frac{\partial^2 T}{\partial z^2} \qquad \text{[Equation 2]}$$

$$d = \sqrt{\chi \tau} \qquad \text{[Equation 3]}$$

In Equations 2 and 3, T, $\chi$, t, z, and $\tau$ represent temperature, heat diffusivity, time, spatial variable, and pulse width of laser, respectively.

In one example embodiment, when a laser pulse with 6-ns width is used for photoacoustic excitation, the thermal diffusion length (d) of 25 nm is obtained for PDMS used as a surrounding medium, which has the thermal diffusivity of $1.06 \times 10^{-7}$ m$^2$/s. With respect to the laser pulse width used for photoacoustic excitation, the thermal diffusion length may be in a range of a few to tens of nm. In the above example, once the optical energy absorbed by the CNTs is converted into heat, then the heat may diffuse by 25 nm from the CNTs to the surrounding volume for 6 ns. When the CNTs are dispersed such that the mean distance between the CNTs is substantially equal to or larger than the thermal diffusion length, the agglomeration of CNTs may be prevented. This simultaneously alleviates the localized heating effect due to the densely packed CNTs that may cause the exceedingly high temperature into the surrounding medium and thus the damage or breakage of composite structure. As a result, the laser-induced damage threshold of photoacoustic generator can be increased by the CNT permeation into the PDMS matrix and then the volumetric dispersal of CNTs that leads to the CNT-to-CNT distance substantially equal to or larger than the thermal diffusion length.

These results mean that the photoacoustic generator (P-C-P1) of Present Example has a laser-induced damage threshold 3.8-fold higher than the conventional generator case that includes candle soots (about 81 mJ/cm$^2$). That is, the photoacoustic generator (P-C-P1) of Present Example can receive and utilize 3.8-fold higher input laser energy without damage than the conventional example using candle soots.

The descriptions of the presented embodiments are provided so that one of ordinary skill in the art of the present disclosure may use or implement the present disclosure. Various modifications to these embodiments will be readily apparent to those skilled in the art of the present disclosure.

The generic principles defined herein may be applied to other embodiments without departing from the scope of the present disclosure. Thus, the present disclosure is not to be limited to the embodiments set forth herein but is to be accorded the widest scope consistent with the principles and novel features presented herein.

We claim:

1. A method for manufacturing a photoacoustic ultrasound generator, the method comprising:
    forming an uncured prepolymer polydimethylsiloxane (PDMS) film on a substrate;
    spraying a solution of light-absorbing nano-particles onto a surface of the uncured PDMS film, and then permeating and diffusing the light-absorbing nano-particles into the uncured PDMS film; and
    curing the uncured PDMS film containing the light-absorbing nano-particles distributed therein to form a composite film of nano-particles and PDMS.

2. The method of claim 1, wherein the light-absorbing nano-particles permeated and diffused into the uncured PDMS film are dispersed such that a mean distance between the light-absorbing nano-particles in the uncured PDMS film is substantially equal to or larger than a thermal diffusion length during the temporal width of an irradiation laser pulse.

3. The method of claim 2, wherein the PDMS composite film is obtained by dispersing the light-absorbing nano-particles in the uncured PDMS film such that the mean distance between the nano-particles is substantially equal to or larger than the thermal diffusion length, and the PDMS composite film has a laser-induced damage threshold that is higher than non-particle-PDMS composite films in which light-absorbing nano-particles are densely packed with a mean distance smaller than the thermal diffusion length.

4. The method of claim 2, wherein the PDMS composite film is obtained by dispersing the light-absorbing nano-particles in the uncured PDMS film such that the mean distance between the nano-particles is substantially equal to or larger than the thermal diffusion length, and the PDMS composite film, in response to being irradiated with a laser pulse width of 5 to 20 ns, has a laser-induced damage threshold that exceeds 300 mJ/cm$^2$.

5. The method of claim 1, wherein the formation of the uncured PDMS film includes the application procedure of a solution of PDMS dissolved in a solvent onto the substrate using drop-casting or spin-coating methods.

6. The method of claim 1, wherein the light-absorbing nano-particles comprise at least one nano-particle selected from the a-group consisting of metallic nano-particles, graphene flake, carbon nanotube (CNT), carbon nanofiber, and carbon nanosoot.

7. The method of claim 1, wherein the method further comprises:
    forming an additional PDMS coating layer by applying a PDMS solution on top of the PDMS composite film; and
    curing the PDMS coating layer.

* * * * *